United States Patent
Kubach (10) Patent No.: US 8,109,871 B2
(45) Date of Patent: Feb. 7, 2012

(54) ENDOSCOPE INTEGRITY TESTER INCLUDING CONTEXT-SENSITIVE COMPENSATION AND METHODS OF CONTEXT-SENSITIVE INTEGRITY TESTING

(75) Inventor: Melissa Kubach, Chesterfield, MO (US)

(73) Assignee: Minntech Corporation, Minneapolis, MN (US)

( * ) Notice: Subject to any disclaimer, the term of this patent is extended or adjusted under 35 U.S.C. 154(b) by 1251 days.

(21) Appl. No.: 11/696,390

(22) Filed: Apr. 4, 2007

(65) Prior Publication Data

US 2007/0238923 A1  Oct. 11, 2007

Related U.S. Application Data (63) Continuation-in-part of application No. 11/371,109, filed on Mar. 8, 2006, now abandoned, which is a continuation-in-part of application No. 11/123,335, filed on May 6, 2005, now abandoned, and a continuation-in-part of application No. 11/123,336, filed on May 6, 2005, now abandoned.

(51) Int. Cl.
  *A61B 1/00*  (2006.01)
  *A61B 1/04*  (2006.01)

(52) U.S. Cl. ........................ 600/101; 600/133

(58) Field of Classification Search .................. 600/101, 600/133

See application file for complete search history.

(56) References Cited

U.S. PATENT DOCUMENTS

| | | | |
|---|---|---|---|
| 4,241,729 A | 12/1980 | Aoshiro | |
| 4,506,544 A * | 3/1985 | Shimizu | ........................ 73/45.5 |
| 4,527,551 A * | 7/1985 | Ishii | ............... 600/132 |
| 4,628,207 A | 12/1986 | Elfert et al. | |
| 4,943,414 A | 7/1990 | Jacobs et al. | |
| 5,031,454 A | 7/1991 | Ams | |
| 5,144,848 A | 9/1992 | Uenishi et al. | |
| 5,211,915 A * | 5/1993 | Monch | ........................ 422/547 |
| 5,243,967 A * | 9/1993 | Hibino | ........................ 600/109 |
| 5,279,799 A | 1/1994 | Moser | |
| 5,317,896 A | 6/1994 | Sheth et al. | |
| 5,402,769 A | 4/1995 | Tsuji | |
| 5,494,530 A * | 2/1996 | Graf | ............... 134/18 |
| 5,614,660 A | 3/1997 | Tanaka | |
| 5,696,686 A | 12/1997 | Sanka et al. | |
| 5,705,737 A | 1/1998 | Liao | |

(Continued)

FOREIGN PATENT DOCUMENTS

JP  3117268  5/1991

(Continued)

OTHER PUBLICATIONS

"Eliminating Fluid Invasion in Flexible Endoscopes," http://www.infectioncontroltoday.com/articles/0c1feat3.html.

(Continued)

*Primary Examiner* — Anhtuan Nguyen
*Assistant Examiner* — Alireza Nia
(74) *Attorney, Agent, or Firm* — William D. Schmidt; Dilworth & Barrese, LLP.

(57) ABSTRACT

Computer systems and software for controlling an endoscope integrity tester. The pressurization and humidity measurement and calculations, and the resulting determination of passage or failure is automated and controlled to eliminate concerns of human error in the detection process. Further, the computer system is capable of adapting its calculations to specific endoscopes and particular testing changes to further improve accuracy by being context-sensitive.

11 Claims, 7 Drawing Sheets

U.S. PATENT DOCUMENTS

| | | | |
|---|---|---|---|
| 5,795,404 A | 8/1998 | Murphy et al. | |
| 5,869,000 A | 2/1999 | DeCato | |
| 5,961,922 A | 10/1999 | Witte et al. | |
| 6,112,578 A * | 9/2000 | Black et al. | 73/40 |
| 6,202,477 B1 * | 3/2001 | Lehmann | 73/49.3 |
| 6,279,383 B1 * | 8/2001 | Balke et al. | 73/40 |
| 6,364,827 B1 | 4/2002 | Irion et al. | |
| 6,408,682 B2 * | 6/2002 | Greszler | 73/40 |
| 6,412,334 B1 * | 7/2002 | Kral et al. | 73/40 |
| 6,425,292 B1 | 7/2002 | Takami et al. | |
| 6,485,684 B1 | 11/2002 | Mapson et al. | |
| 6,491,625 B1 | 12/2002 | Newton et al. | |
| 6,545,523 B1 | 4/2003 | Takami | |
| 6,572,819 B1 | 6/2003 | Wu et al. | |
| 6,618,603 B2 * | 9/2003 | Varalli et al. | 600/345 |
| 6,923,758 B2 | 8/2005 | Ishibiki | |
| 6,986,736 B2 * | 1/2006 | Williams et al. | 600/101 |
| 7,018,331 B2 * | 3/2006 | Chang et al. | 600/182 |
| 7,276,023 B2 * | 10/2007 | Annecke | 600/101 |
| 2004/0139789 A1 * | 7/2004 | Masters | 73/49.2 |
| 2005/0056081 A1 * | 3/2005 | Gocho | 73/40 |
| 2006/0006931 A1 | 1/2006 | Hsieh et al. | |
| 2006/0045798 A1 | 3/2006 | Wu et al. | |
| 2006/0069306 A1 | 3/2006 | Banik et al. | |
| 2006/0196250 A1 | 9/2006 | Gocho | |
| 2006/0224042 A1 | 10/2006 | Jackson et al. | |
| 2006/0252990 A1 | 11/2006 | Kubach | |
| 2006/0252991 A1 | 11/2006 | Kubach | |
| 2006/0293564 A1 | 12/2006 | Nishiie et al. | |
| 2007/0008160 A1 | 1/2007 | Nagai et al. | |

FOREIGN PATENT DOCUMENTS

| | | |
|---|---|---|
| JP | 2001245839 | 9/2001 |
| JP | 2006191988 | 7/2006 |
| WO | WO2005026683 | 3/2005 |

OTHER PUBLICATIONS

Olympus DSD-201/DSD-201LT Endoscope Disinfectors, 2003.
"The New Sterrad RX System," www.sterrad.com.

* cited by examiner

ENDOSCOPE INTEGRITY TESTER INCLUDING CONTEXT-SENSITIVE COMPENSATION AND METHODS OF CONTEXT-SENSITIVE INTEGRITY TESTING

CROSS REFERENCE TO RELATED APPLICATION(S)

This application is a Continuation-in-Part (CIP) of U.S. patent application Ser. No. 11/371,109, filed Mar. 8, 2007 and now abandoned, which is in turn a Continuation-in-Part (CIP) of U.S. patent application Ser. No. 11/123,335 and U.S. patent application Ser. No. 11/123,336, both of which were filed May 6, 2005 and are now abandoned. The entire disclosures of all the above documents are herein incorporated by reference.

BACKGROUND

1. Field of the Invention

This disclosure relates to the field of integrity testing for endoscopes, in particular to computer systems and software to carry out such integrity testing.

2. Description of the Related Art

As medical science has advanced, it has recognized that the ability of diagnostic evaluation procedures to detect various maladies early in their development provides one of the primary tools in preventing adverse outcomes. At the same time, highly invasive procedures, even if effective at their intended task, introduce their own dangers. Invasive procedures require a long time to heal, are expensive, and can result in additional costs due to extensive hospitalization, additional therapies to recuperate, and lost productive time. In an attempt to provide for medical services at reasonable cost to most of the population, it is desirable to have maladies detected, and treated early and to provide both the detection and intervention using procedures which are as minimally invasive as possible to speed up recovery time and reduce risks introduced from the performance of the procedure.

To provide for many minimally invasive procedures, medicine has seen a dramatic rise in the use of endoscopic instruments. Traditionally, extensive invasion of the body was required to allow a surgeon to see where he was working as well as to allow the body to admit his hands, which are relatively large instruments, during a procedure. The use of endoscopes provides for an alternative solution in both cases. Endoscopes are long slender medical instruments which can be inserted through a relatively small orifice in the body. With advanced optics, an endoscope can allow a doctor to see structures without the need for invasive surgery and often better than his normal eyesight would permit. Further, by including specially designed and small-sized instruments, a doctor's hands need not be admitted into the body of the patient to perform procedures which allows for still further reductions in the need for large entry points. Endoscopic surgical tools have advanced greatly in recent years allowing a doctor to examine internal structures, take biopsies, and even perform some types of surgery. While many endoscopic procedures utilize one or more small incisions, others utilize natural body openings such as the mouth, nose, ear, rectum, vagina, or urethra. The latter type of endoscopes are particularly useful when related to disease of the gastrointestinal tract or reproductive system and because they are inserted in naturally occurring openings, are considered to be minimally invasive.

An endoscope is generally used in a procedure by being inserted into the opening (whether natural or artificial) by a doctor trained in its use. The endoscope is then guided to the area to be examined through the use of an external control on the end of the endoscope remaining outside the body. In some cases, such as when the colon is being examined, the path taken by the endoscope is itself evaluated. In some alternative cases, the endoscope is maneuvered to reach a particular destination which is to be examined or operated on. In either case, to facilitate the movement of the endoscope, the endoscope is generally a long flexible tube sized and shaped for the particular procedure to be performed and will be capable of being guided through body structures, without damage, through what is often a convoluted path.

The endoscope will include instruments related to its function and the particular procedure being performed. These instruments will generally first provide for visual or other detection apparatus and related image recordation. These instruments will serve first to allow the operator to guide the instrument, but also to provide records of what was done and to store particular images for later evaluation. The tube may also include ports on the portion external to the body which allow for medications, water, air, or instruments to be inserted externally and passed through the endoscope to the point where the internal end of the endoscope is located. The instruments can then extend from the internal end of the endoscope to allow for the performance of medical activities. These instruments will generally be controlled externally while what they are doing is monitored using the detection apparatuses. Endoscope procedures may include, but are not limited to, biopsies of material; the introduction of medical agents, irrigation water, or apparatuses; cleaning of an area for improved visual characteristics; and some surgical procedures.

In most endoscopes, either the natural orifice through which it is inserted defines a maximum size of the scope, or the scope is generally desired to be as small as possible to minimize the size of an incision necessary to insert it. At the same time, it is necessary for the endoscopes to include control mechanisms outside the body, as well as generally sophisticated cameras or other imaging apparatus, and ports for, or inclusion of, medical application delivery devices. Further, electronics and systems to allow for signals to be transported from the control device outside the body to the tip of the endoscope which is inaccessible inside the body are necessary. Hook-ups to external computers to provide for interpretation of data signals are also generally required. All of these sophisticated systems make endoscopes quite expensive and sophisticated devices. Further, the popularity of endoscopic procedures means that most medical providers need a relatively large number of endoscopes, even of similar type, in order to be able to provide for all the procedures they are used for.

Even while use of endoscopic instruments is minimally invasive, without proper care, they can still transmit disease. It is necessary that endoscopes be well cleaned and sterilized after each use to prevent transfer of potentially dangerous agents between patients. Endoscopes will also often operate in what can be considered a wet environment or other environment where body fluids are in contact with the exterior of the endoscope which is generally a form of rubber tubing. Cleaning and sterilization systems also often utilize liquids in cleaning. Because an endoscope's sophisticated design uses a high number of components which can be adversely effected by moisture, generally an endoscope will be sealed from external fluid invasion by having its components sealed inside the flexible plastic or rubber sleeve. Components which are not sealed during use are alternatively sealed by caps during cleaning as the entire instrument can be inserted in liquid during the cleaning process.

The plastic or rubber sleeve can fail over time and develop holes or fractures from repeated use and general wear and tear. Further, improper handling or use of the scope can damage the sleeve. If the sleeve develops holes, cracks or other points of failure, it can allow the introduction of moisture to the internal components of the endoscope. If this occurs inside the body of a patient, it may allow microorganisms to travel with the endoscope. More commonly, however, the failure will allow for cleaning agents to get inside the endoscope. Any of these intrusions to the endoscope can be dangerous to the endoscope. Even a single drop of water inside the endoscope can result in sensitive electronic devices becoming damaged and the endoscope becoming unusable. Further, the intrusion of even a small amount of body fluid can result in a non-sterile instrument.

Beyond the possibility of fluid intrusion from cracks or breaks in the coating, most endoscopes are required to have some access to internal structures to allow for external devices, such as computers, to operate in connection to the internal components. In use, these ports are generally plugged by a connector or similar device. After use, a sealer cap or related device is generally placed in the ports to seal them from external invasion. These caps can also develop holes, seals can break down, or protective covers may be incorrectly installed. Any of these situations can also lead to fluid invasion of the endoscope.

To clean endoscopes between procedures, generally the endoscope is first disconnected from associated computer apparatus, is wiped down and open channels are suctioned and washed to remove most of the material on the scope. The scope is then sent to be cleaned. As cleaning requires specific immersion or saturation of the endoscope with liquid materials, it is important that the scope be checked for leaks prior to this cleaning; otherwise a leak could admit cleaning materials and damage the endoscope. Traditionally, leaks were tested for by a technician who would access the internal structure of the endoscope, and if a leak was detected, connect an air source and introduce air to raise the internal pressure of the scope above the ambient to inhibit fluid invasion during cleaning and prior to repair.

In the most basic test methodology, the scope was immersed in fluid (usually water) while held at a positive pressure and left there for a period of time. During this time, the technician would look for bubbles rising from the endoscope indicating loss of air from the internal structure. This methodology was fraught with problems. In the first instance, placing the structure in water tended to produce bubbles. Further, solutions used to initially clean the endoscope could themselves create bubbles when interacting with the water. Still finally, movement of the scope in the water could conceal or introduce bubbles.

To try and get around this problem, systems were introduced which allowed the internal area of the endoscope to be pumped to a particular pressure. The user would then watch a gauge or indicator to determine if the pressure decreased over a period of time. Other systems tried to automate the provision of air, and the monitoring of pressure. One such system is described in U.S. Pat. No. 6,408,682, the entire disclosure of which is herein incorporated by reference.

Integrity testers for endoscopes which rely on purely human control to determine if a leak exists are fraught with problems. The human user would pump up the internal area of the endoscope to about the desired pressure, but pumps could be unreliable and gauges may not actually indicate true pressure. The user then reviewed what was usually an analog gauge for any movement of the needle downward indicative of a leak. While fairly large leaks were readily noticeable, smaller leaks may not be noticed as the ability to notice them would be dependent both on the user's ability to read a gauge, which could have a large amount of wiggle, and the willingness of the user to watch the gauge long enough to make sure that any loss is detected.

Automated systems generally were not much better. While these systems allowed for machine monitoring of the internal pressure which allowed for more accurate calculation, the systems generally relied on volume changes which are inaccurate due to the rubbery nature of the sleeve material. Further, the systems did not provide for processor control related to humidity testing in addition to pressure testing.

SUMMARY

Because of these and other problems in the art, described herein, among other things, are computer systems and software for controlling an endoscope integrity tester. The pressurization and measurement calculations and the resulting determination of passage or failure is automated and controlled by a computer control system to eliminate concerns of human error in the detection process. Further, the computer control system is capable of adapting its calculations to specific endoscopes and particular conditions of testing to further improve accuracy.

Described herein, among other things, is a method for testing the integrity of an endoscope, the method comprising: obtaining an endoscope; supplying gas to an air enclosure which includes an internal volume of the endoscope to pressurize the air enclosure; sealing the air enclosure; measuring the pressure of the gas in the air enclosure over time; detecting an first rate of decrease in air pressure; recognizing a second rate of decrease in air pressure, the second rate being less than the first rate; discarding the first rate; and comparing the second rate to a predetermined target rate to determine if the second rate is sufficiently high to indicate a leak in the endoscope.

In an embodiment, the method further comprises: instructing a user to manipulate the endoscope while the air enclosure is pressurized such as, but not limited to instructing manipulation of endoscope buttons or knobs which causes movement of endoscope tubing.

In an embodiment of the method the predetermined target rate is stored in a computer memory. In another embodiment, in the measuring, the pressure of the gas is at least 4 $lbf/in^2$.

In an embodiment, the method further comprises: identifying the endoscope as having been tested previously. The predetermined target rate may then be determined based on at least one previous test of the endoscope.

In a still further embodiment, the method further comprises: placing the endoscope in a holding device, which may comprise a holding bin having a mat on its base, the mat including a plurality of fingers, prior to the step of measuring.

There is also described herein a method for testing the integrity of an endoscope comprising the steps of: obtaining an endoscope to be tested; retrieving a plurality of calibrating humidity values from a plurality of prior endoscope tests from a memory; obtaining an environmental humidity value from air external to the endoscope to be tested; manipulating at least a portion of the combination of the plurality of calibrating humidity values and the environmental value to produce a target humidity value; supplying a gas to an air enclosure which includes an internal volume of the endoscope to be tested; venting the gas in the air enclosure to a humidity detector; determining the level of humidity in the vented gas; and comparing the level of humidity to the target humidity value to determine if the level of humidity in the endoscope is sufficiently high to indicate fluid invasion into the endoscope to be tested.

In an embodiment of the method, in the retrieving, the plurality of prior tests do not include a prior test of the endoscope to be tested while in an alternative embodiment, the plurality of prior tests only include prior tests of the endoscope to be tested.

In an embodiment of the method, in the manipulating, an average of calibrating humidity values is determined. This may be a weighted average of calibrating humidity values is determined using the environmental humidity value as the weighting factor or another calculated average.

There is also described herein, a computer implemented method for performing endoscope integrity testing, the method comprising: providing to a computer controlled endoscope tester an endoscope to be tested; the tester identifying the endoscope as having been tested previously; the tester retrieving from a memory, a retrieved value of property of air determined from at least one prior test of the endoscope; the tester testing the endoscope by supplying air into an internal enclosure of the endoscope; the tester determining a current value of the property of air from the air supplied into the internal enclosure of the endoscope; the tester comparing the current value to the retrieved value; the tester determining if the comparison indicates a compromise of integrity in the endoscope; and the tester supplying the determination to a user.

In an embodiment of the method the retrieved value is an average of all prior tests of the endoscope or the property of air is pressure or humidity. In another embodiment of the method the identifying includes, identifying a serial number associated with the endoscope.

In another embodiment the method further comprises: recording the current value.

There is also described herein, a computer system for testing endoscopes, the system comprising: at least one sensing means; memory means; and processing means coupled to the sensing means and the memory means; the processing means being capable of: identifying an endoscope to be tested as having been tested previously; retrieving from the memory, a retrieved value of a property of air determined from at least one prior test of the endoscope; testing the endoscope by supplying air into an internal enclosure of the endoscope; determining a current value of the property of air from the air supplied into the internal enclosure of the endoscope; comparing the current value to the retrieved value; determining if the comparison indicates a compromise of integrity in the endoscope; and supplying the determination to a user.

DESCRIPTION OF PREFERRED EMBODIMENT(S)

Figure 1:
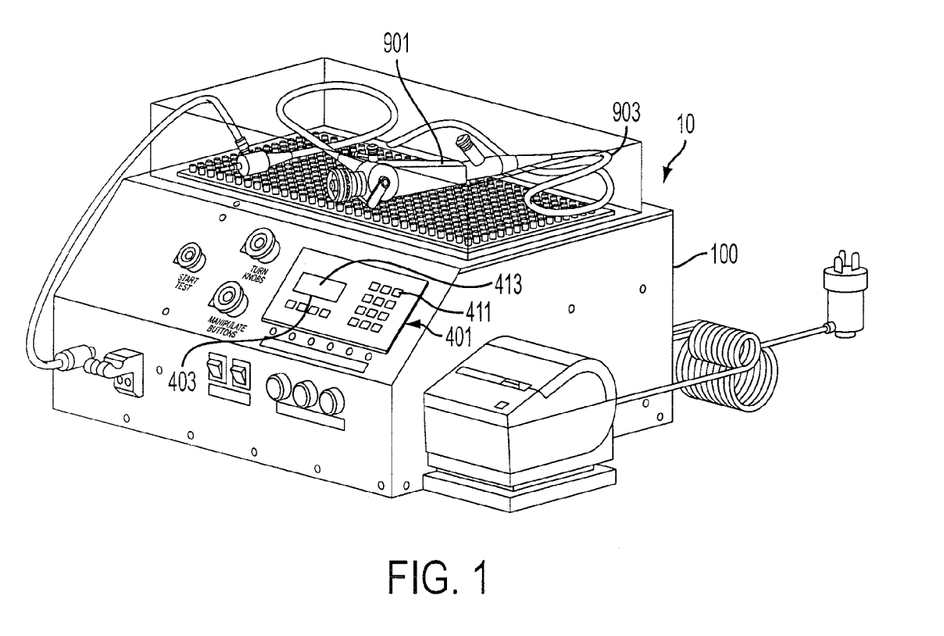
FIG. 1 shows a front prospective view of an embodiment of a device for testing the integrity of endoscopes.

FIG. 1 depicts an embodiment of an integrity tester (10) for use to determine the integrity of endoscopes (901). That is, to determine if the internal area is sealed or if there are openings which could allow fluid invasion. This particular embodiment of integrity tester (10) is described in additional detail in U.S. patent application Ser. Nos. 11/123,335 and 11/123,336 which are parents of this instant case and incorporated herein by reference. This is not the only type of integrity tester that the computer control systems (301) discussed herein may operate on, but merely provides an exemplary embodiment.

Without going into great detail as to the operation of an integrity tester (10), the integrity tester (10) will generally perform at least one of a pressure measurement or humidity measurement on the endoscope (901). Pressure measurements will generally involve pressurizing the internal space inside the endoscope (901) (generally along with some external space to form a single area called an "air enclosure") to test for leaks of pressurized air outwards. Humidity testing, on the other hand, utilizes the possibility of wetness (along with exterior air) being pulled into a leaky endoscope (901), or already being present inside a leaky endoscope (901) as an alternative test for leaks and a test for potentially damaging conditions.

Generally, the integrity tester (10) comprises a housing (100), which will serve to house the various components. Generally, the components will include the computer control system (301), an air compressor or other air source, a pressure sensor, and a humidity sensor. There will also be a series of valves which allow for air to flow into or out of the endoscope and to form an air enclosure, which includes the internal structure of the endoscope. The air enclosure, therefore, is designed to be a predefined volume including the internal space of the endoscope (901). In this way air pressure within the endoscope (901) can be monitored without placing a pressure sensor physically within the sleeve (903).

The endoscope (901) is attached to the tester (10) for testing. The integrity tester (10) of FIG. 1 is designed to test both pressure and humidity tests and the discussions herein will focus on computer control systems (301) for performing a pressure test followed by a humidity test, however one would understand how to utilize this teaching to perform one or the other test alone or to alter the order in which tests are performed.

The tester (10) of FIG. 1 will generally be controlled by a computer control system (301) which is intended to provide for automated control of the pressurization and testing of the endoscope (901), and the evaluation of output of the pressure and humidity sensors to determine if there is a leak in the endoscope (901). The computer control system is preferably capable of adapting its calculations to specific endoscopes or particular conditions of testing to further improve accuracy. In this way, the testing is context-sensitive in that the computer control system (301) can measure each endoscope in a context of prior endoscope (901) measurements. This context may be prior measurements of the same endoscope (901), such as to allow for compensation of a particular endoscope's (901) peculiarities, or may be in the context of multiple endoscopes (901), such as to detect shifts over time of environmental testing conditions.

Figure 2:
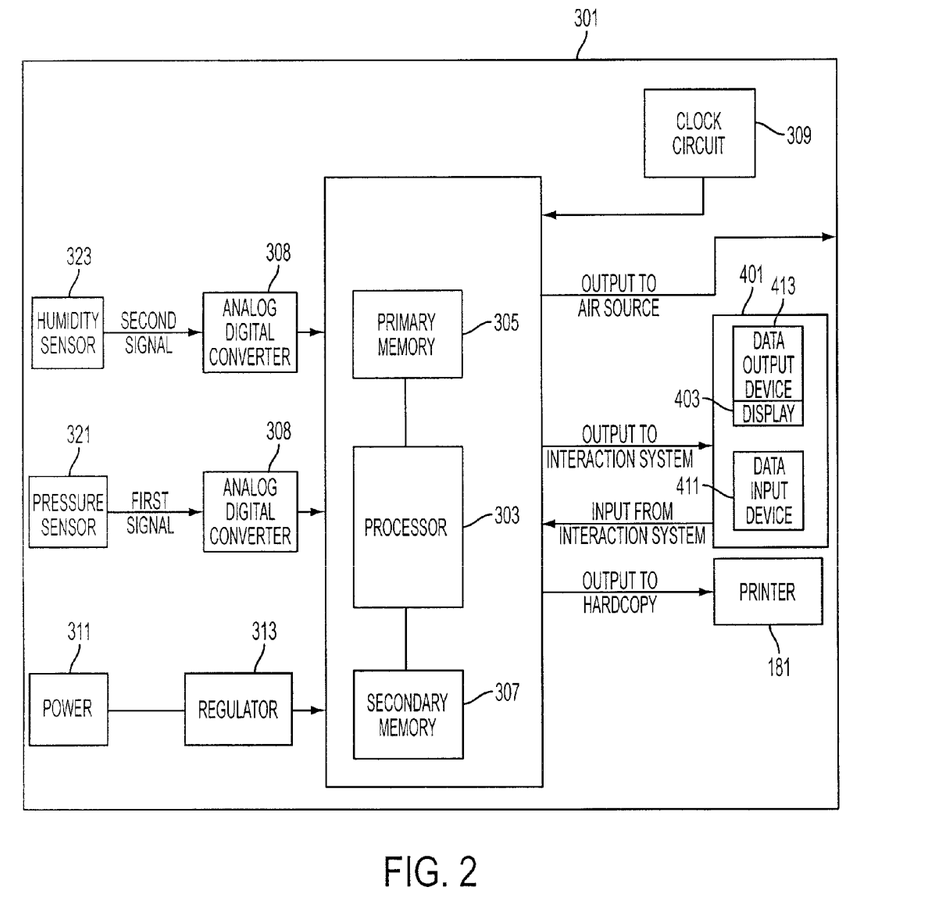
FIG. 2 shows a block diagram of a computer control system.

An embodiment of a control system (301) is shown in block diagram in FIG. 2. The computer control system (301) will generally comprise a processor (303) which will perform calculations and manipulations on the various data provided to it as well as generally instruct other components. This may include sending or receiving signals to or from those other components. The processor (303) may be of any type known to those of ordinary skill in the art and may, in an embodiment, comprise a general purpose processor (303) running software programs provided in an attached primary memory (305), or may comprise a single purpose processor (303) specifically programmed or built to control the integrity tester (10).

The computer control system (301) will also include an interaction system (401) which generally includes a data input device (411) and a data output device (413). The data input device (411) can comprise a numerical keypad, keyboard, buttons, switches or other structures which can be manipulated by a user so the user can provide input into the computer control system (301). In an embodiment, data input can also be obtained from a microphone or other audio source, or other type of device. The data output device (413) will generally be any form of display (403) known to those of ordinary skill in the art for providing information from the computer control system (301) to the user. This information may comprise results of tests or other output of the processor (303), or requests for information from the user, or other types of information. In an embodiment, the display (403) will comprise a screen such as, but not limited to, an LCD screen capable of providing a visual indicator of information through the use of standard characters or symbols. The display (403) may also include indicators or lights which serve as alternative visual indicators. The display (403) may also additionally or alternatively comprise devices capable of generating audible or other non-visual signals.

The computer control system (301) also includes a pressure sensor (321) and humidity sensor (323) which are capable of generating signals indicative of current air pressure and current air humidity in the air enclosure. In the depicted embodiment, these devices generate analog signals and therefore the computer control system (301) also includes analog to digital converters (308) to provide the data output from these sensors in a manner that is understood by the processor (303).

The computer control system (301) will also include associated primary memory (305) which is used for operations during the testing. In an embodiment the memory will include computer software providing instruments for the operation of the processor (303). The primary memory (305) may also be used for the storage of testing parameters or variables which are used by the computer control system (301) for testing the endoscope (901). The primary memory may also be used for storage of processor (313) output.

In another embodiment, there is also included a secondary memory (307) which can be used to both store testing software or variables for use by the processor (303) and which can also be used for storage of information generated by the processor (303). Often the secondary memory (307) will provide for storage of test results for later retrieval. In an embodiment, the secondary memory (307) may be designed to be removable so that information can be transferred from one tester (10) to another tester (10) or an alternative device. Generally, when this disclosure refers to reading or writing a value to memory either primary memory (305) or secondary memory (307) could be used, if present.

The computer control system (301) may also include systems for connecting other computing devices to the tester (10), both via networks or by direct connection. This can allow for external memory devices, diagnostic tools, programming devices, input or output devices, or other devices to be temporarily or semi-permanently attached to the tester (10). In an embodiment, this is done to allow for multiple testers (10) to operate together in a network fashion. In such an embodiment, elements of the computer control system (301) may be provided as network resources (e.g. a central processor or memory may be shared by all testers) to provide for improved computational performance and decreased downtime.

The computer control system (301) also includes a hard copy generation device (181) such as a paper printer which is used in addition to the data output device (413) which is intended for providing more transient output. The computer control system (301) will also generally include some form of clock circuit (309) to provide for both traditional date and time information along with clock signals to time testing activities and a power input source (391) and possibly power regulator (393) as shown.

In a preferred embodiment, the computer control system (301) will rely on computer readable code or instructions which are held in memory to provide for its operation. In general, this software will be capable of instructing the various components of the tester (10) to perform steps such as those shown in FIG. 3 and to perform calculation on received values and tests against known testing parameters. In an alternative embodiment, the processor (303) will be hard wired to perform the necessary calculations. Regardless of which method is used, the computer control system (301) provides instructions to control operation of the components of tester (10). This allows for the tester (10) to generally perform all tests in an automated manner and to rapidly and repeatedly perform calculations. The computer control system (301) also eliminates a large amount of measurement error as the human element is removed from interpreting the received results in the first instance.

Figure 3A:
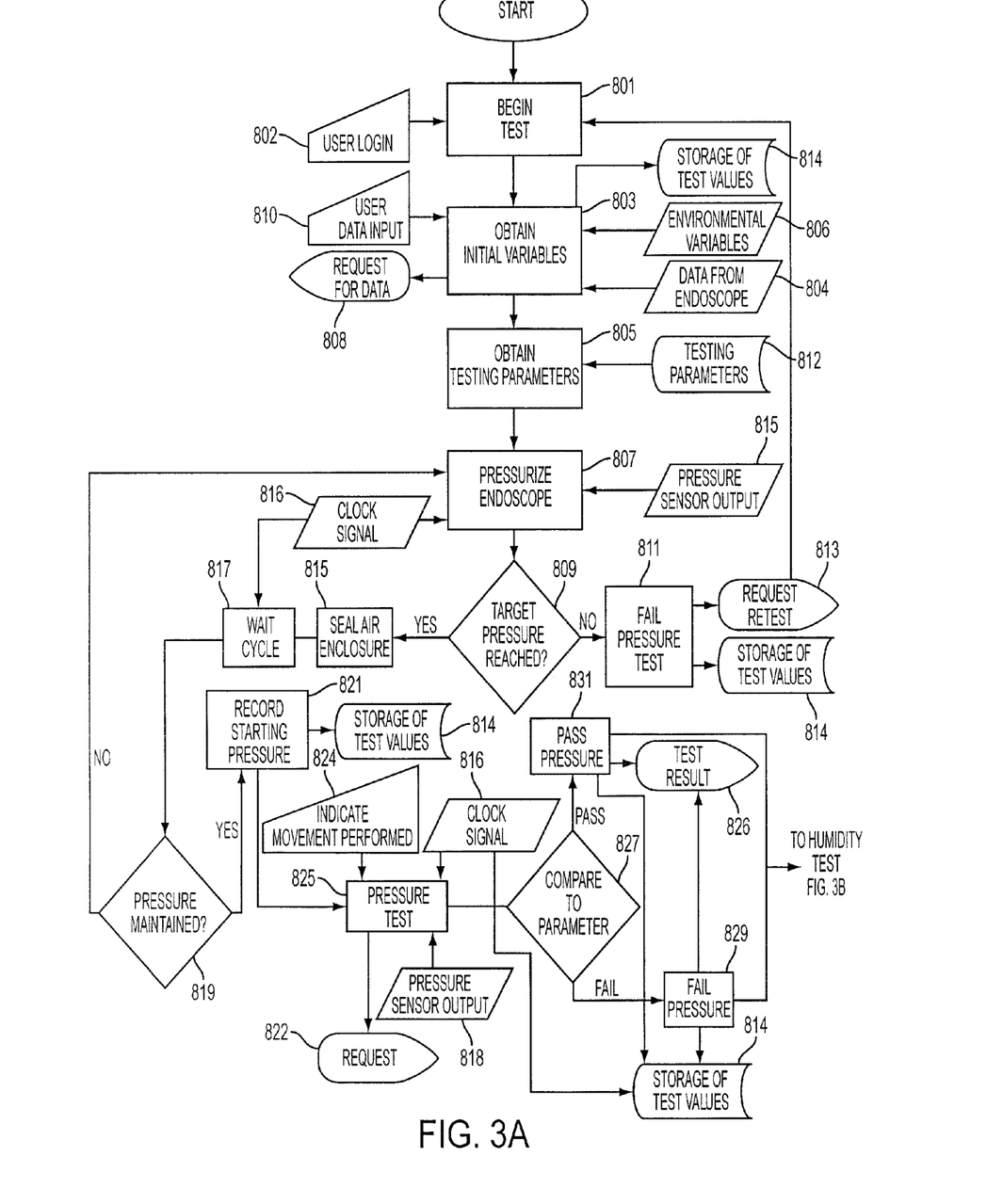
FIG. 3 shows a flowchart of the steps in one method of operation. The process is divided between FIG. 3A and FIG. 3B.
Figure 3B:
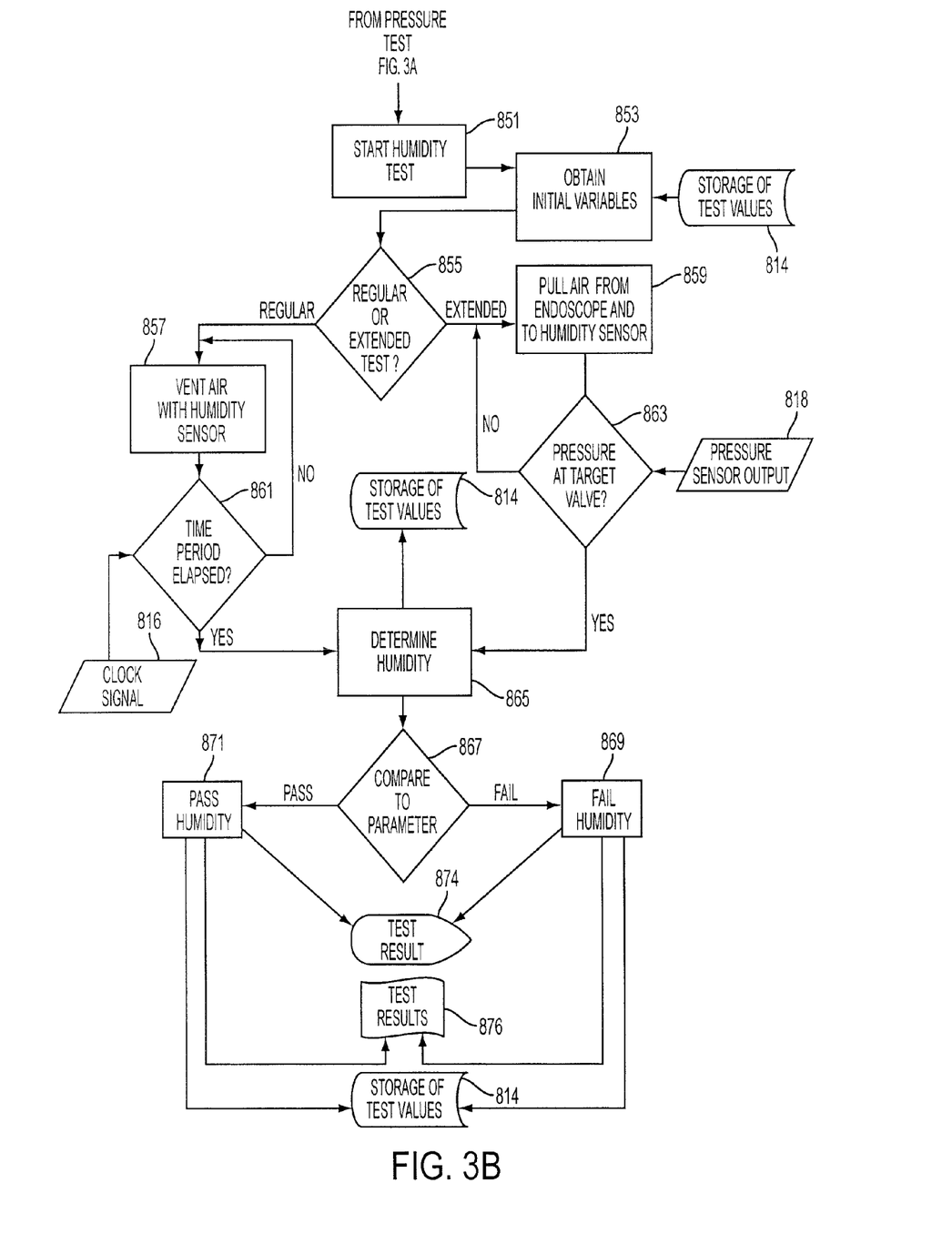
Figure 6:
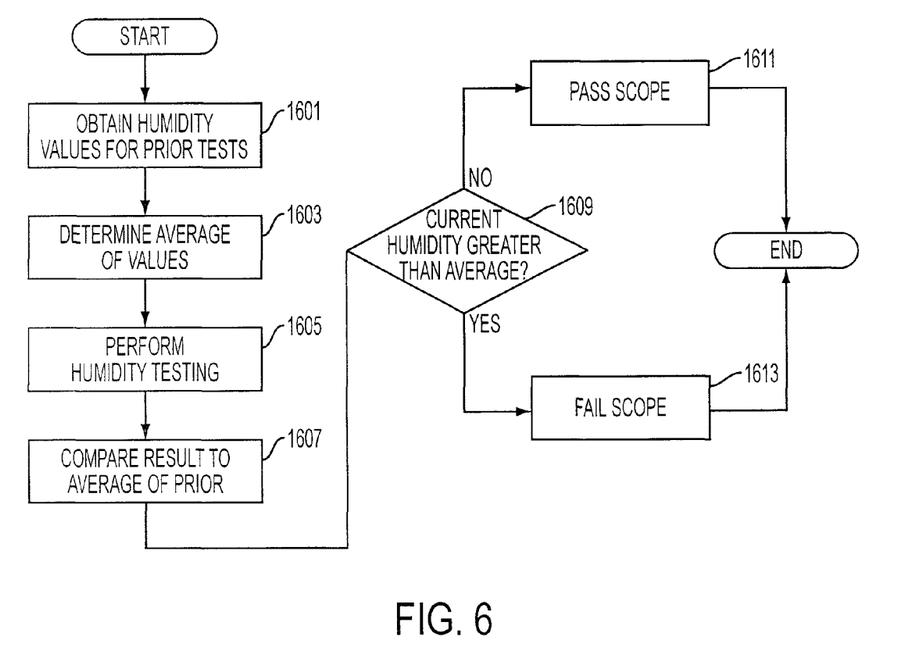
FIG. 6 provides a flowchart showing how to get a compensating humidity target.
Figure 7:
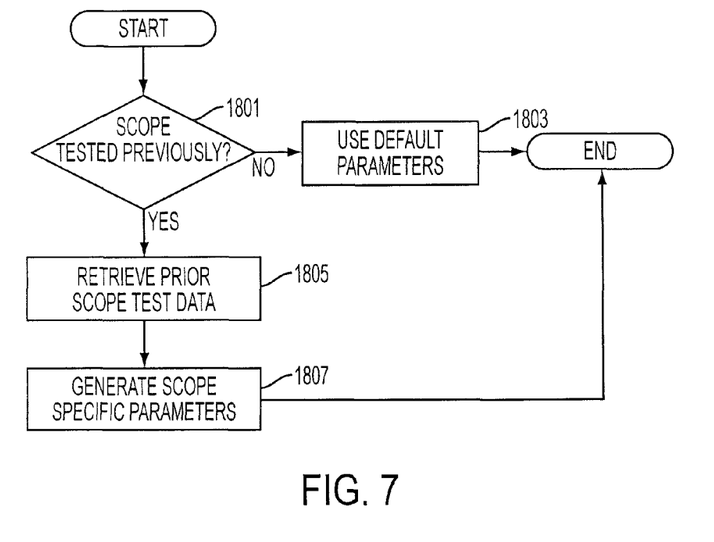
FIG. 7 provides a flowchart showing how to have scopes be remembered by the testing apparatus for future testing compensation.

The computer processing of the endoscope (901) information begins once the user has connected the endoscope (901) and the computer control system (301) has been provided with power. One embodiment of a testing operation is shown in FIG. 3 and some details of particular methods are shown in FIGS. 6 and 7. At the start of FIG. 3, the user will commence an interaction with the integrity tester (10) to indicate that a test is to be begun in step (801). This can be as simple as pressing a start or power button to initiate the testing process. There may, in a first embodiment, be a general login process (802) which occurs prior to allowing the system to commence testing. This may be desirable if the system is used by multiple users or is allowed to power off between tests. The initial system login (802) may include user identification information or other information that will be used for a multiple of tests before the system is powered off or otherwise placed in a standby situation. This may be used for security purposes or for quality control reasons, amongst other things. Once this initial login process is completed, the tester (10) is prepared to test endoscopes. As the tester (10) will generally rely on the user for indications of when an endoscope (901) is to be tested, the computer control system (301) will generally enter a standby mode until instructed that a testing cycle is desired by the user. This indication may be provided by the user pressing a start button indicating that they wish the tester (10) to begin the testing cycle.

Generally, after the testing cycle is initiated in step (803), the computer control system (301) will request, in step (808) via the data output device (413), the user provide initial variables regarding this testing cycle via the data input device (411) in step (810). These variables will generally provide for information related to identifying this particular testing cycle and the endoscope (901) to be tested. The user may also provide various other indications during this initial data gathering phase.

In most cases, at least some information will be requested from the user (808) so that output can be associated with the specific endoscope (901) and testing cycle and any desired modifications to the standard testing routine can be loaded. Often the software will request an identifier (such as a serial number or related identifier) so as to associate the information gathered with the particular identifier when stored for easier searching and retrieval. In an alternative embodiment, specifics about the type of endoscope (901) to be tested (either by entry of identifiers or by having the user select from options) or the hookup being used may be requested. These pieces of information may be used by the processor (303) in selecting a particular set of testing parameters to be used in this testing cycle from a number of testing parameters. Alternatively, the variables may be used to compute the actual testing parameters.

In an alternative embodiment, instead of requesting information from the user (808), the computer control system (301) may obtain the information directly from the endoscope (901) by sending a query to various sensors or other devices that can return information about the endoscope (901) as shown in step (804). This may be from electrical connections made during the connection of the endoscope (901), or via wireless mechanisms. For instance, in an embodiment, the endoscope (901) can identify itself to the tester (10) when it is connected by sending a packet of information to the processor (303) when the connection is made.

In a still further embodiment, the processor (303) can send out additional queries to obtain more information outside of the user or endoscope (901). For example, in an embodiment, the computer control system (301) may request various data related to air collected from within the endoscope (901) prior to commencing any testing to estimate a temperature within the endoscope (901), for example. Alternatively, the processor (303) could at this time also issue queries to gather environmental information such as humidity or temperature in the room in which the tester (10) is located as indicated in step (806). This external request for information need not be performed before the automated portion of the testing cycle begins but may be performed at any time during the testing alternatively or additionally. Alternatively, the processor (303) can request information from memory (305) or (307) related to the endoscope (901) to be tested as discussed later. Any values collected in step (803) may be stored in step (814).

Once these initial variables have been received by the processor (303), the processor (303) will generally select the testing parameters in step (805). The testing parameters (812) generally are data and computations that will be used by the processor (303) to determine if the endoscope (901) should pass or fail any test to be performed on it. The term is therefore used herein to generally refer to the information that needs to be calculated or loaded by the processor (303) to perform the desired testing. This may include, but is in no way limited to, any or all of the following: length of time in which to perform the testing, maximum or minimum allowed values of pressure and humidity; pressure to be used to commence testing, or expected values of pressure and humidity over time-based criteria. The selection of testing parameters (812) may comprise the processor (303) performing mathematical calculations using the variables and various preset stored values to determine the parameters of the analysis, or may comprise loading of a profile of prepared values to test the endoscope (901) against. Such profiles will generally comprise a set a testing parameters to be used, or of values which are used to generate the testing parameters, depending on the type of endoscope (901) being tested and the desired tests to be performed.

Different endoscopes (901) can have different parameters. The processor (303) may also take into account environmental or other conditions. For instance, certain endoscopes (901) may require more air to inflate, may naturally lose more air through their fittings, or may react differently to temperature. By selecting parameters of expected performance, the tester (10) can attempt to minimize error in the testing process. In effect, the processor (303) determines the testing parameters that are most likely to indicate that this endoscope (901) either does or does not have a leak based on the variables measured during the testing cycle. For instance, if a larger stronger endoscope (901) is being tested, the computer control system (301) may inflate the endoscope (901) to a greater pressure than if a small, easily damaged, endoscope (901) is being tested. Further, an endoscope (901) which is hot may be allowed to have a longer stabilization period, or an endoscope tested in a wetter climate may be allowed to include higher natural humidity.

In an embodiment, the profile of testing parameters may be specifically based on prior performance of the same endoscope (901) in the same tests and therefore its expected performance in this test if there has not been any change to it. These prior results may be used directly as parameters, or a number of them may be mathematically manipulated to form the parameters. Such manipulation may include, but is not limited to, calculating average and standard deviation. An embodiment of a flowchart showing a test utilizing parameters based on prior performance of the same endoscope (901) is provided in FIG. 7. In this embodiment of test parameter selection, the step of obtaining testing parameters (805) occurs generally as follows. The processor (303) will utilize the identifier for the particular endoscope (901) provided in step (803) and determine if the endoscope (901) has previously been tested by this tester (10) or by another tester (10) the stored data of which this tester (10) has access to in step (1801). If the endoscope (901) has not been tested previously, there is no past data on the endoscope (901) to use to influence the testing parameters, so the system will select default parameters in step (1803). The default parameters may simply be a preset test to be performed on endoscopes (901) which have not been tested before, or may comprise a default starting point which is combined with other inputted data to generate a specific profile for this endoscope (901). As a previously untested endoscope (901) will often be a new endoscope (901) this may also influence the parameter selection.

If the endoscope (901) has been tested previously, the computer control system (301) will retrieve the prior test results in step (1805) from memory (305) or (307). The prior test results may then be modified or combined with the outside environmental variables of step (806) and any other information available to the processor (303) to generate a scope specific testing profile in step (1807). This scope specific profile is basically a customized profile for the way the endoscope (901) is expected to perform in this testing cycle based on how it has previously performed in prior testing cycles weighted based on changes specific to this cycle which may have an effect. While the use of such prior testing results could occur in any fashion, a number of possible methodologies should be apparent.

In an embodiment, the tester (10) will store all the prior results of prior tests. In the situation where all prior tests have shown the endoscope (901) to have maintained its integrity, this group of tests can provide for a floating baseline over time of the score the endoscope (901) usually obtains when passing. If the endoscope (901) in the current test scores within this range, or a small deviation from it, when under similar environmental and testing conditions, this will generally be treated as a pass. If the testing conditions are different or other conditions are different (for instance if the scope is much hotter than normal), the system can provide for calculation compensation based on the predicted value from other tests. For instance, if the scope normally stabilized in a certain range of time which is longer than the average for scopes of this type and the scope is hotter than normal, the processor (303) may provide for a longer stabilization time without triggering a potential fail situation. Alternatively, the range of allowed deviation from the standard may be increased in such a situation.

When using previously stored information about the same endoscope (901), the information may include any number of prior tests, averages or other mathematical computations based on a plurality of tests, or even recognition of changing circumstances. Further, generally the more each endoscope (901) is tested, the more data on its performance that will be available and the more information which may influence the parameters. For instance, if an endoscope (901) had previously been tested 100 times without failure, but failed the 101st test, upon the 102nd test, earlier test results (e.g. the first 50 tests) may be used to provide parameters on the ground that since it has been fixed, the endoscope (901) should be able to meet more demanding test requirements, comparative to when it was new as opposed to those of when it had been in long relatively continuous use. Had the scope have passed test 101, however, an average of the 50 most recent test outcomes may be used in test 102 to allow for flexibility increases or other changes to the endoscope (901) which may have been introduced over time to weight the profile. Alternatively, specific tests performed at similar temperature and humidity conditions to the current ones can be selected from amongst all the prior tests to try and compensate for environmental changes.

While the above specifically discusses using prior data for pressure testing, such prior data can be used in pressure testing, humidity testing, or both depending on the desired operational mode of the device. Further, the user can select different types and even different selections of prior data to use in different embodiments of the tester (10) as opposed to the processor (303) selecting the values according to various criteria.

While the selection of a profile of testing parameters and/or the computation of testing parameters (812) based on the input variables and based on the specific endoscope (901) is desirable in an embodiment, it is by no means required and in the simplest case the testing parameters (812) may be fixed across all endoscopes (901). In this embodiment, therefore, the testing parameters (812) would be the same in each case, however, the testing parameters (812) may or may not be altered by environmental readings or other variables. This embodiment is desirable where the system is likely to be testing only similar endoscopes (901) under similar conditions repeatedly or where there is little concern for loss of accuracy due to variance between endoscopes (901) being tested.

Once the testing parameters have been obtained by the processor (303), generally from memory, the processor (303) will next send instructions in step (807) to an air compressor or other air source to commence providing air into the internal structure of the endoscope (901). This filling will commence the actual testing phase of the cycle in step (807). In order to obtain a pressure as close to the target pressure (generally in the testing parameters) as possible, the processor (303) will generally continuously query a pressure sensor (815) using clock signal (816) until the target pressure is as close as possible to the desired pressure.

In order to improve accuracy of the pressure test, the pressure inside the endoscope (901) is generally as high as possible, without risk of damage to the endoscope (901). Traditionally, pressure provided to the endoscope (901) has been limited to just a couple of pound feet per square inch as that is all a hand pump can easily generate. Even in water bath measurements where air compressors were used, pressures simply above the weight of the water on the endoscope (901) (generally around 3 $lbf/in^2$) were used. Higher pressures are beneficial as they provide for a greater degree of accuracy in endoscope (901) testing. With a higher pressure it is more likely that a hole in the endoscope (901), which may be held closed by the flexible nature of much of the endoscope (901) sleeve, will be forced open by the air pressure. Air at a higher pressure is therefore more likely to escape from a small hole held shut by surface tension, gravity or similar forces making it more likely that small holes are detected. Further, for a hole of equal size, the pressure internal to the endoscope (901) will often change more dramatically at a higher pressure than at a lower pressure because more air is forced out with the higher pressure. It is usually preferred that the air pressure in the air enclosure and therefore in the endoscope (901) be raised to a pressure at or above 4 $lbf/in^2$ and generally less than 8 $lbf/in^2$ but that is by no means required. It is often preferred that the pressure be about 4.5 $lbf/in^2$.

The particular target pressure for the endoscope (901) is generally one of the selected testing parameters and therefore may be at least in part determined by the nature of the attached endoscope (901) and other input of collected variables. In this way an endoscope (901) which can better tolerate higher pressures may be exposed to higher pressures. Further, the target pressure can also be modified to compensate for environmental factors, such as the endoscope's (901) temperature, which can effect the endoscope's (901) interaction with the air by altering its potential energy and/or by effecting its pressure, volume, etc.

In an embodiment, the processor (303) will continuously monitor the output of a pressure sensor in step (807) as air is added to the air enclosure and thus the endoscope (901) in step (807). If over a pre-selected window of time the air pressure has not reached the target pressure in step (809), the processor (303) can determine that the endoscope (901) fails the pressure test in step (811) as it is sufficiently leaky to be unable to pressurize. Alternatively, a failure to reach pressure could indicate a problem in a connection or a defective component. To address this situation, a retest may be suggested to the user via the data output device (413) in step (813) telling the user to disconnect and reconnect the endoscope (901) and retest.

Depending on the embodiment, if there is a failure due to an inability to reach target pressure, the integrity tester (10) may continue to perform the humidity test discussed below, may alter the humidity test parameters such as to perform an extended humidity test, or may terminate the test process as the endoscope (901) has already been failed and requires service regardless. In the embodiment of FIG. 3, a failure to reach pressure results in storage of an impossible pressure value in step (814) which the processor (303) recognizes as clear fail.

In addition to determining if an endoscope (901) can reach the target pressure, the computer control system (301), in an embodiment, may measure the length of time it takes to bring the endoscope (901) up to pressure and/or the rate that the pressure increases. The first pressure test may therefore involve this calculation of time to bring the air enclosure up to pressure. If it takes too long to bring the endoscope (901) up to pressure or if the rate is too low, even if the endoscope (901) can reach the target pressure in the window of time, the integrity tester (10) may determine that a leak exists and fail the endoscope (901). Alternatively, the rate of pressurization may also be used by the processor (303) in later calculations to determine if a pressure loss is unacceptable. If the endoscope (901) takes a longer time to pressurize than is expected and was hot, for example, the processor (303) could determine that the sleeve (903) is expanding significantly and therefore provide for a longer wait period to allow it to stabilize. The processor (303) may also alter the testing parameters to use a lower target pressure to prevent possible damage from deformation at a higher pressure based on such a reading.

If the endoscope (901) is able to brought up to pressure within the window of calculation and at a sufficient rate of speed, the integrity tester (10) will begin the pressure maintenance testing to determine if the pressure is maintained over time. The test generally begins when the air enclosure (and thus the endoscope (901)) is sealed from known outside air sources or vents in step (815). Once sealed in step (815), the computer control system (301) will disable the air input and initiate a wait cycle in step (817) to allow the air enclosure's pressure to stabilize over a period indicated by the clock signal (816) before initial pressure values are taken in step (821).

In the wait period of step (817), the system will allow for the endoscope (901) to stabilize under pressure. The endoscope (901) comprises a generally rubber or plastic sleeve (903) whose integrity for holes is to be tested. This sleeve (903) is subject to stresses from the internal air pressure which is applied to it and may deform or expand due to that pressure as its structure is generally not rigid. This deformation is also more likely to be present if the endoscope (901) is at a warmer temperature (which it often is as it is tested after being cleaned and/or sterilized) or if the endoscope (901) is more flexible due to its design. Temperature can introduce a number of issues because as the internal air heats (absorbs heat from the sleeve (903)) the air pressure may increase, while at the same time the sleeve's (903) increased flexibility may increase the volume internal to the sleeve (903) decreasing the air pressure. The waiting period may be determined based on the temperature or other characteristics of the endoscope (901) that are part of the profile or may simply be a fixed preset.

The processor (303) will generally utilize the signals (816) of the clock circuit (309) to determine if the waiting period has elapsed in step (817). At the end of the waiting period, the computer control system (301) will generally check to see if the pressure has been maintained at an acceptable level in step (819) through the waiting period to begin testing in step (821). If not, the computer control system (301) may reactivate the air source and flow more air into the endoscope (901) or may allow pressure levels to decrease by venting some air. In another embodiment, the computer control system (301) may simply take readings utilizing the altered starting pressure value. In effect, this initial waiting period (817) does not utilize pressure difference present to determine if there is a leak, but instead attempts to make sure that a false reading will not be given in later testing due to effects present in any endoscope (901) under the particular conditions. In the event that the stabilization resulted in a need to alter the internal air composition, there may then be an additional waiting period to allow further stabilization, or the testing may simply continue to step (821).

Generally, a commencement of testing activities after a single waiting period is preferred as it does not allow for the computer control system (301) to become stuck in a situation where a leak is interpreted as stabilization behavior. Therefore, the computer control system (301) will now record the starting pressure in step (821) sending that value to memory in step (814). This value is generally around the target starting pressure based on the testing parameters. The computer control system (301) will monitor the pressure by querying the pressure sensor for readings (818) on a regular basis via step (825). Generally, the pressure will be monitored for a fixed period of time based on the output (816) of the clock circuit or for a fixed number of measurements.

While the pressure is maintained in the endoscope (901) by maintaining the seal on the air enclosure, the control system (301) may periodically enter into hold phases during the testing and indicate that the user should perform various manipulations on the endoscope (901). In the depicted embodiment, a user is instructed to perform a particular manipulation on the endoscope (901) by indications on the data output device (313) in step (822). Once the user has performed the manipulation, they indicate to the computer control system (301) via the input device that the manipulation has been performed in step (824) which indicates to the computer control system (301) to exit the holding pattern and allow the test to continue.

In the depicted embodiment, user interaction in step (825) relates to the user being instructed to manipulate the knobs and/or buttons of the endoscope (901). Once so instructed, the user is expected to pick up the endoscope (901) at its control portion and manipulate all the knobs, buttons, etc. of the endoscope (901). This will provide for movement of the endoscope (901) in all directions. The movement will help to reveal tears or holes in the sleeve (903) which may only be apparent when the endoscope (901) is positioned in a particular fashion. In particular, movement will cause the rubber at the moving portion to be stretched or flexed as it may do during the course of both a procedure and cleaning. Further, it tests for leaks in seals related to manipulation controls.

The user will also generally manipulate buttons related to various operations of the endoscope (901). This may serve to move the endoscope (901) in the same way as the manipulation of the knobs did, but generally, and often more importantly, will test for any holes in the button seals. Once the user has completed the requested movements, the user will indicate to the control system (401) that they have completed the manipulation in step (824). The computer control system (301) may then continue the test. If the user does not indicate that the endoscope (901) has been manipulated within a certain time window after the instruction is sent, the computer control system (301) will generally time out and indicate an error condition because the manipulation was not indicated to have been performed.

It should be apparent to one of ordinary skill in the art that the manipulation of buttons and knobs provides for benefits to the integrity tester's (10) accuracy. In particular, in order to manipulate buttons or knobs, the endoscope (901) is moved at least once during testing, this may provide for a hole to be revealed and allowed to open which was held shut by the initial placement of the endoscope (901). This can occur for instance, if the endoscope (901) principle tubing is placed so that it is coiled or where one portion overlaps another. Further, the manipulation allows for components which can be damaged by interaction with an operator to be tested and to be tested under conditions that the endoscope (901) may experience during use or cleaning. Therefore, if a hole exists in a portion of a button cover designed to flex, but that hole is only revealed when the material is flexed, it is detected by the flexing and can be fixed before it presents a major concern. While the pictured embodiment provides that the manipulation be performed by the user, this is by no means required and in an alternative embodiment robotic or similar manipulation systems may alternatively be used to automatically perform the manipulation.

Once all manipulations have been indicated to be performed, the testing will generally continue until the time period indicated by clock signal (815) is completed or a preliminary test is determined sufficient to indicate failure during the period of step (825). This period of testing would generally have been selected either by initial user variables or as part of the testing parameters and will generally be between one and five minutes. The period may be calculated so that the selected length of the complete test includes the time of manipulation, or may be selected to count time excluding the time of the expected manipulation.

To determine if sufficient pressure is lost within the time period to indicate a leak, the computer control system (301) in step (827) may use a variety of calculation and evaluation techniques. Regardless of how well components are sealed, there will always be some slight pressure loss due to natural bleeding of components and additional stretching of some components during the testing cycle. Further, handling of the endoscope (901) can alter the pressure values slightly by potentially altering the internal volume during the handling. The computer control system (301) will generally, therefore, have as part of the testing parameters an acceptable pressure loss for the endoscope (901). This acceptable value may relate to testing on known endoscopes (901) which are known to be undamaged to determine an expected or acceptable loss of air pressure for undamaged endoscopes (901).

In an embodiment of the pressure determination, a time pressure average of a plurality of pressure measurements within sub periods of the time period of testing are used in the calculation to compute a raw pressure loss over the time period or any sub periods. In an embodiment, noise and other factors are removed from this determination to provide for a smoothed indication of pressure where small individual changes that are likely caused by factors other than an actual leak are ignored or averaged out. For instance, a slight increase in pressure may be expected when the device is manipulated, leading to a small downward spike when the manipulation is completed. The change in pressure over the period of the test, or any portion of the test, is then determined and adjusted for the measurement accuracy of the pressure sensor. The result is then compared against an allowed or threshold change rate in step (827). If the calculated change is greater, the endoscope (901) is failed in step (829) as more pressure has been lost than would be expected if the endoscope did not have a leak; if less pressure than the threshold is lost, the endoscope (901) is passed in step (831). These values are generally reported to the user in step (826).

While raw pressure loss over time provides for one beneficial way of measuring for possibly integrity problems, in an alternative embodiment, the system actually compares a rate of pressure loss over the measurement period as opposed to a raw pressure loss. In such an embodiment, the computer control system (301) also does not use the pure pressure drop for determination of acceptable or unacceptable pressure change, but instead looks at the rate of pressure drop. This allows the system to recognize that the endoscope (901) will always lose some pressure and that the amount lost may actually meet a net loss target, but the rate may be sufficiently low to indicate that there is not a leak. The issue is that an endoscope (901) with a leak will lose pressure faster than one which is instead simply losing pressure due to natural pressure loss over time.

In an embodiment which measures loss rate, the computer control system (301) will look for a leveling out of the rate of loss, at a point which is still sufficiently above the atmospheric pressure to indicate that the endoscope's (901) internal pressure has stabilized above the atmospheric pressure, while still showing a sufficient decrease in rate to indicate that the initial stabilization period has passed.

Figure 5A:
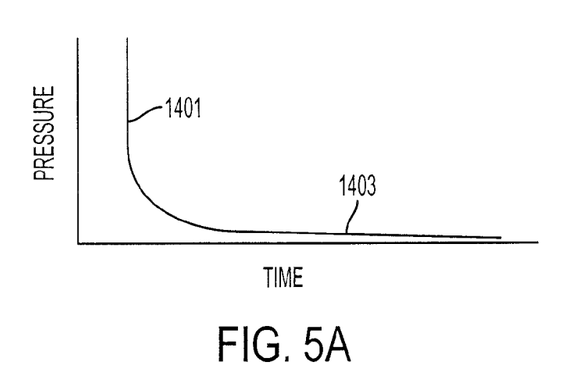
FIG. 5 shows three graphs of representative pressure loss curves which can indicate loss or maintenance of integrity.

FIG. 5 provides for three graphs which show possible loss curves for different types of scopes. In the first curve (FIG. 5A), the pressure inside the scope rapidly falls off from an inflated pressure in section (1401) which would represent the stabilization period to a pressure right around the pressure external to the scope where it levels off in section (1403). This type of curve would generally indicate a scope with a major leak which is incapable of maintaining pressure and in need of repair as the endoscope (901) effectively never stabilized at a pressure above the ambient.

Figure 5B:
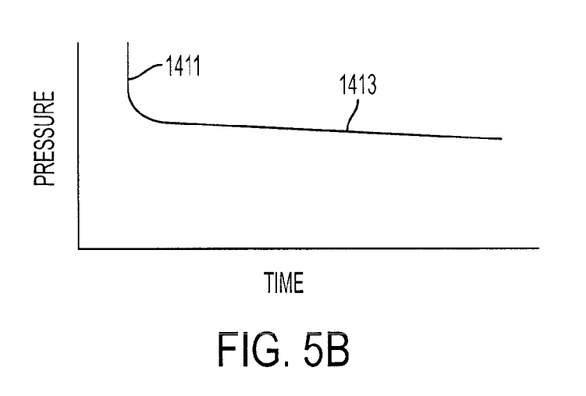

The curve of FIG. 5B provides for a different situation. In this situation, the pressure rapidly falls off in section (1411) again indicating stabilization behavior but then flattens out in section (1413) at a pressure level significantly above that of the atmosphere. This decrease in rate would be the expected behavior of an endoscope (901) which has not had its integrity compromised by a hole. As should be apparent from FIG. 5B, there is still pressure loss in section (1413) as indicated by the continuing downward slope, but the rate is sufficiently low (the slope is sufficiently horizontal) to imply that the continued pressure loss is not due to a hole. In FIG. 5B the endoscope (901) cannot necessarily maintain the initial pressure and needs to adjust, but once an equilibrium point is reached, the rate of loss of pressure decreases sharply, and while the endoscope (901) is still losing pressure, it is losing it at a much decreased rate.

Figure 4:
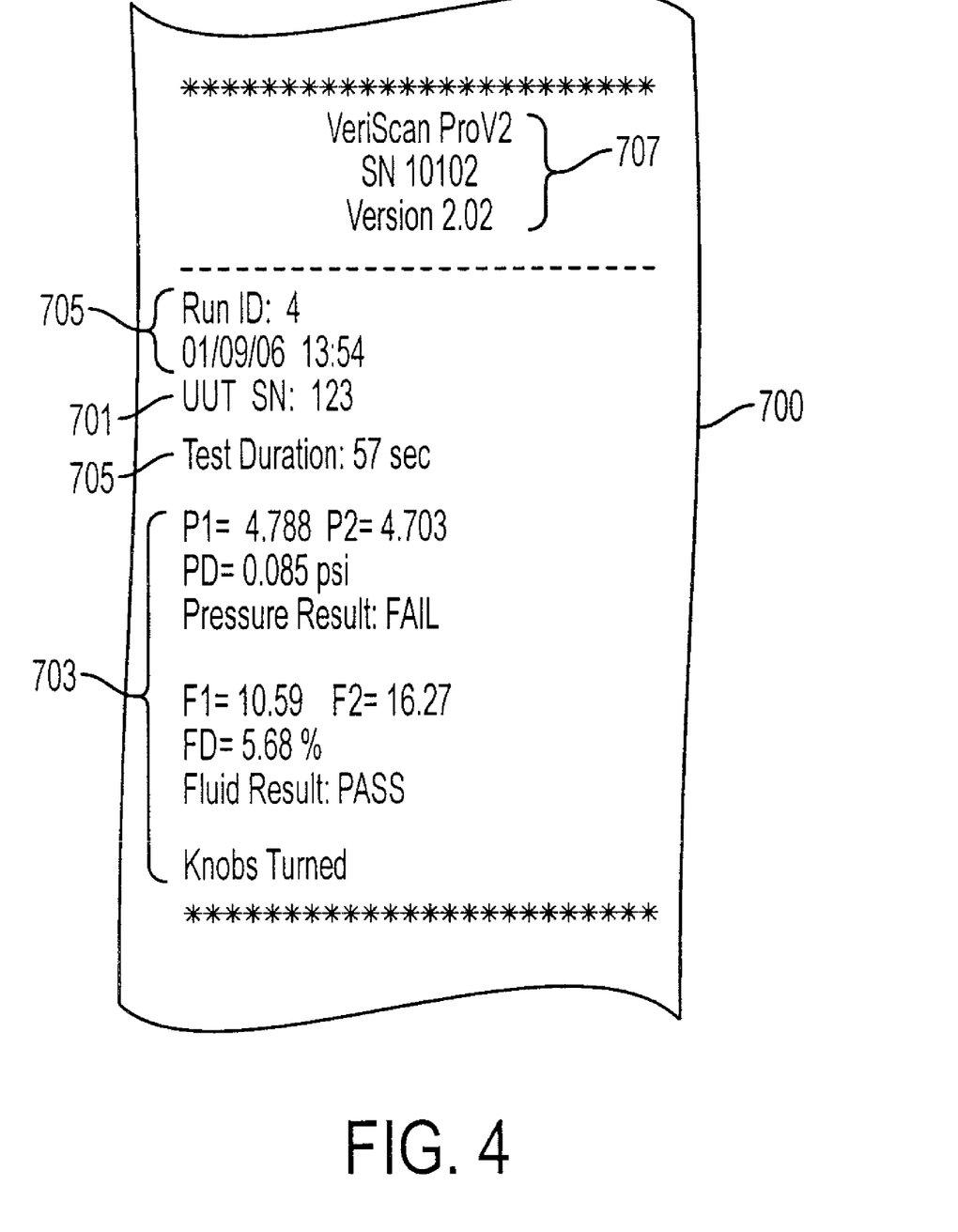
FIG. 4 shows an embodiment of a printout of results from an endoscope test.
Figure 5C:
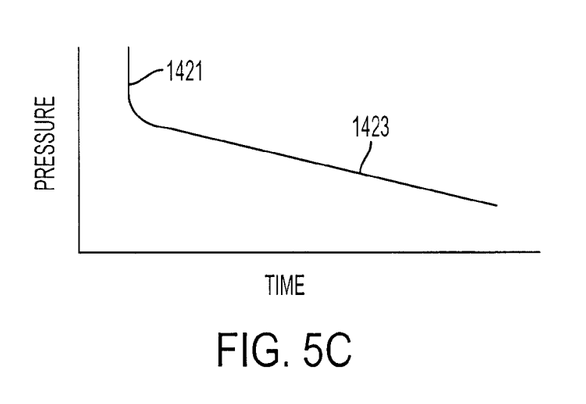

This is contrasted with FIG. 5C which provides for the case of an endoscope (901) with a hole. Like in FIG. 4B, the first section (1421) shows a rapid loss of pressure as the endoscope (901) reaches a stable equilibrium pressure. However, once this equilibrium is reached, the endoscope (901) loss rate decreases in section (1423). However, the endoscope (901) is unable to maintain the pressure because of the hole and while the pressure loss rate is decreased in section (1423), it is still too high and the endoscope (901) is clearly leaking air.

The three graphs or similar ones can be utilized by the computer control system (301) to provide for more accurate determinations of when there is a hole which is leading to air loss. In particular, the processor (303) can evaluate the rate of the air loss (slope of the line) to determine when loss transitions from being due to the endoscope (901) searching for equilibrium pressure, to either loss from a hole or natural loss simply to be expected even when integrity is still being maintained.

To carry out this analysis, the computer control system (301) will first generally recognize that there will be an initial rate of decrease after the air enclosure is sealed. It will, therefore, wait until the section (1401), (1411), or (1421) was passed by looking for a leveling of the rate. Upon determining that the air pressure is beginning to level out, the system will examine what the current pressure is. If the pressure is sufficiently high that the pressure may be maintained and is not indicative of a large hole (FIGS. 5B and 5C), the computer control system will commence the measurement period.

During the measurement period, the system may be examining the rate of air loss in an instantaneous fashion, or may wait until the end and evaluate the change over time. Regardless of which method is used, the rate of decrease of the second section (after sterilization) measured will be used to determine if the loss is unacceptably high and indicative of a hole. The rate of loss can take into account specifics such as the age of the endoscope (901) and other prior tests for loss as discussed previously. Generally, such a determination will occur by comparing the current rate of the air loss after stabilization to a selected maximum allowed rate.

In an embodiment, if an endoscope (901) has a rate of loss on par with the rate of loss it has on prior tests, that can be indicative that the endoscope's (901) integrity has not been compromised. If the endoscope (901) had been previously evaluated or repaired and was known to not have any holes at the times of prior tests this context-sensitive determination can provide improved accuracy. If the rate has increased dramatically over prior tests, that can be indicative of a hole and the endoscope (901) can be put aside to be further evaluated. Further, because of the fact that rate of loss, and not raw air loss values are being examined, the endoscope (901) can stabilize at different values depending on environmental conditions and testing conditions at the time of the particular test without the computer control system (301) necessarily being less accurate in its determination.

The ability to compensate for changing environmental or other conditions, and changes to the endoscope over time, provides parameter selection which is context-sensitive and can help improve accuracy in calculation and detection of scopes which actually are damaged.

The processor (303) will also generally store values in step (814) related to the pressure test in memory in step (814). Generally these values will include the starting and ending pressure readings and the pressure change (which can be calculated by the processor (303) from the starting and ending pressure or could have been calculated instantly). The pass/fail result will generally also be stored. A clock value related to the time the test took to perform and the time the test was performed may also be stored. In an embodiment, additional information may be stored (or the addresses of such information may be maintained for a longer time) if the endoscope (901) fails than if it passes. In this way, diagnostic information related to the failure may be available to help repair personnel determine the cause of the failure.

Once the integrity tester (10) has determined that the endoscope (901) has passed or failed the pressure test, the next test (humidity test) determines if the endoscope (901) includes any fluid within its internals and may provide a double check for holes. The integrity tester (10) may start the humidity test automatically following the conclusion of the pressure test, or may request input from the user about whether to commence the humidity test in step (851). If the test is to go forward, the humidity test may be performed in a regular or extended fashion as indicated in step (855). Generally prior to the humidity test, the processor will determine the baseline humidity in step (853) from the stored values (814). As the air pumped into the endoscope (901) was generally dried by a desiccator prior to entering the endoscope (901) as part of the process, it should still be dry and will generally be dryer than the outside air. If the system includes a hole, however, the dry air (which was under pressure) will often have escaped out the hole during the pressure test and environmental air will be pulled through the hole into the endoscope (901) during the humidity test. Alternatively, liquid may have already entered the endoscope (901) and will be vaporized by the dry air provided under pressure, providing more humidity to the air.

The baseline for environmental humidity is generally established as part of the selection of initial variables as discussed above and is pulled from memory in step (853). Alternatively, in step (853) the processor (303) may issue queries for the initial values. To test for humidity inside the endoscope (901), air from within the air enclosure, which includes the air in the endoscope (901), will be vented into contact with the humidity sensor in step (857). At the start of the venting, the air inside the air enclosure is generally at higher pressure than any air in the vent path. If there was little loss of pressure, the air in the air enclosure will generally push itself to the humidity sensor, however, it is often desired to pull additional air from the air enclosure. In this situation, the software may instruct an air withdrawing system (which may be the air source operated in reverse in an embodiment) to suck or pull air from inside the air enclosure. This type of operation is indicated in step (859) of the extended test shown in FIG. 3. Alternatively, the air source can push air into the air enclosure to create a flow of air through the air enclosure. In such a situation, the processor (303) may continuously monitor the pressure (818) in the air enclosure in step (863) to prevent a positive or negative pressure situation from potentially damaging endoscope (901) components. The time of performance of the test may be based on simple venting time from the clock signal (816) as is shown performed in the standard test in step (861) or may be based on the resultant pressure in the air enclosure as indicated in step (863) of the extended test. As shown in the embodiment of FIG. 3, the nature of the air collection may depend on the type of humidity test desired. In the extended test side, air is purposefully pulled from the endoscope (901). This can be desirable if it is already known that the endoscope (901) failed the pressure test. Such failure can indicate insufficient air pressure remaining in the air enclosure to get a valuable reading. Therefore, the different test selected may be based on the testing parameters, or may be selected based on already taken readings.

If there is fluid in the endoscope (901), the fluid will usually be at least partially vaporized by the pressurized air previously applied and be pulled into contact with the humidity sensor during the testing. The humidity sensor (121) will then register that the humidity level of the air is of a certain level in step (865) following a possible wait period. That level is indicated to the processor (303) in step (867) where it is compared with testing parameters. Generally, if this level is at or above a trigger amount determined from a baseline humidity selected based on the testing parameters and/or environmental readings as compared in step (867), an indicator of fluid invasion is triggered in step (869). Alternatively, if the humidity is sufficiently low, the humidity test is passed in step (871).

While the air provided to the endoscope (901) is essentially dry, it is likely that air previously in the endoscope (901) included some humidity and therefore an amount based on the environmental baseline, instead of based on the air having absolute dryness, is preferably used as a trigger. In an alternative embodiment, an absolute dryness level may be used or an independently chosen level of humidity may be selected (such as that based on the humidity of a dry scope for example). The output of the humidity test may be used to indicate fluid invasion of the endoscope (901), as indicated, or may alternatively or additionally be a secondary leak test. In the second instance, a humidity may be detected which may indicate that environmental air is invading the endoscope (901), but no actual fluid is believed to have entered yet.

In a still further embodiment, the computer control system (301) may utilize a threshold humidity value based on an environmental calculation which takes into account changing humidity conditions over time at the testing location. In this embodiment, the computer control system (301) determines a flexible humidity baseline which is determined based on humidity results obtained from prior testing runs of the tester (10). In an embodiment, the testing runs are not for the same endoscope (901) that is currently being tested, but are instead based on an average or other mathematical manipulation of prior runs of all endoscope (901) within a certain time period, or numerical range of testing (e.g. the last 200 tests). What this will allow the computer control system (301) machine to do is slowly adjust the baseline for changing environmental conditions as those conditions slowly change at the tester's (10) location.

For example, it is well known that inside buildings, there is generally a decreased humidity during winter months (as furnace systems dry air and there is less water evaporation) than during summer months (when furnaces are not active and environmental water evaporation is greater). However, humidity levels do not suddenly shift between winter and summer levels but will generally slowly oscillate over time.

In operation, the computer control system (301) when opening in an environmental compensation mode may operate as indicated by the flowchart of FIG. 6. The computer control system (301) in this embodiment will begin by determining the change in humidity among a large number of previous test runs (for instance 200) in step (1601). This calculation may be the humidity of the endoscope's (901) test results compared to the environmental humidity (the difference in humidity) or may be a raw humidity calculation from the endoscopes (901). These would generally be both pass and fail runs, however, only pass or fail runs could be used in an alternative embodiment. The numbers will then generally be averaged in step (1603) to provide for a comparison value. In addition to averaging, step (1603) could also include other mathematical manipulation such as, but not limited to, computing standard deviation or determining other values representative of the variance in the numbers. The system will then perform the humidity testing in step (1605) on the current endoscope (901) and compare in step (1607) the result for the current endoscope (901) to the value(s) obtained in step (1603). In the determination step (1609), so long as the humidity value of the current endoscope (901) (whether absolute or comparative) is within an area of tolerance based on this calculation, the endoscope (901) is passed as indicated by step (1611). A sufficient deviation from the expected value would result in an indication of failure in step (1613). The area of tolerance may also change depending on humidity. For instance, if the environmental humidity is higher, smaller changes may be triggered as failures as the increased moisture in the air is more likely to trigger a concern.

While the above focuses on a calculation based in change in humidity, the absolute humidity of the scope may also be used. In particular, the level of expected humidity may be determined for a large number of endoscopes (901) based on recent tests performed by the tester (10). This can be logical as the air fed into the endoscopes (901) is generally of a similar controlled humidity level. However, air that may be pulled into the endoscope (901) through a leak or provided by the tester may include some variance in humidity over time depending on changes to external humidity or may change in humidity due to absorption of moisture or other factors having to do with environmental air being internal to the endoscope (901) prior to testing. Humidity indications above this context-sensitive value by more than a tolerable amount may trigger an indication that humidity presence is not due simply to more humid air being within the endoscope (901), but by aerosolization of water internal to the endoscope (901), or humid external air being pulled in through a hole.

If the humidity is sufficiently low in the tested air, insufficient humidity is detected and, it is determined by the computer control system (301) that there has been no fluid invasion, or at least not sufficient fluid invasion to generate concern. If humidity testing also does not indicate a hole, the endoscope (901) passes humidity testing and the humidity "pass" result is indicated in step (871) otherwise the endoscope (901) is failed in step (869). These outcomes are displayed to the user in step (874). Values related to the humidity testing such as the internal humidity value, environmental humidity value and the difference in values along with the determination of the control system regarding pass or fail of the endoscope may again be stored in memory (814) after completion of the test. Once both tests are completed and the outcomes calculated, the tester (10) has effectively completed the test process.

In the depicted embodiment, the integrity tester (10) will be attached to a printer or other hardcopy generator (181). This allows the operator to print out an indication of what happened during the test (including pass, fail and other details) to keep with the endoscope (901) or with a centralized records system in step (876). In the event of a failure requiring repair, the printout can be put with the endoscope (901) and provided to those responsible for repair.

In an embodiment, the printout is provided automatically and includes the information that was stored in the memory related to the testing of the endoscope (901) just tested. This information will generally be provided in an easily readable form and may be provided on a paper tape. An embodiment of such a paper tape printout is provided in FIG. 4.

The paper tape (700) includes the information stored for this endoscope (901) and may include the identification information (701) of the endoscope (901). The tape (700) may also include an indication of the level of passage or failure (703), if desired, to indicate if the endoscope (901) failed dramatically or only just failed. The tape (700) may also include date and time information (705) along with indications of the name and version of the software and/or processor (303) being used (707) to make sure that if there are any updates which may have not been used when the test was done. The tape (700) may also include which type of tests were performed.

The tape (700) above simply provides for simple reference information and will often be placed with the endoscope (901) prior to its next use so that the next user can confirm that the endoscope (901) is ready for use and has been recently tested. In the event of a failure by the endoscope (901) of one or both tests, additional information may be stored and/or printed by the computer control system (301) to provide for more information. For example, depending on the type of failure (pressure or humidity) and the severity of the failure, the repair technician may therefore have more of an idea of what needs to be repaired, or if additional tests need to be performed to determine the exact nature of necessary repair. If a loss of pressure is sudden and related specifically to the period where knobs or buttons were being manipulated, for example, the printout (700) may make such an indication so as to provide the repair technician with an indication that the problem is probably associated with one of those areas. This can also provide for improved repair response by localizing a point to first examine.

In the event that the endoscope (901) failed a humidity test, this information can also be provided. In this case, the repair technician can know that the endoscope (901) needs to be disassembled and dried. Further, if no pressure loss was detected, but a humidity test was failed, repair personnel may perform more exacting pressure tests on the endoscope (901) utilizing more exacting testing parameters to determine if a very small, but important hole, exists, or if a hole may exist in conjunction with a knob movement or button press which was not accurately detected, for instance if a technician had skipped the step or only performed it a rudimentary level but indicated it had been performed. Alternatively, the technician can test the integrity of cap fittings or similar devices to try and locate a possible point of fluid entry that may not necessarily indicate an integrity problem, but instead simply a misassembled endoscope (901) at some point in time.

In addition or alternatively to providing for a printout (700) of testing results, the integrity tester (10) may store values in local memory or may be connected to a computer network such as, but not limited to, an intranet, extranet, internet, or the Internet so as to act as a client or server on the network. In this situation, the information on the specific test need not be stored in local memory but may be reported to a central data repository. For instance, if an endoscope (901) is indicated as failing, a notice may be sent to repair personnel to expect to receive the endoscope (901). Any or all data collected by the control system (301) during the test may also be forwarded and provided to repair personnel or stored for evaluation in a central location to determine what may be wrong with the endoscope (901). Such information can also be used to monitor the status of a hospital's, or other user's, stockpile of endoscopes. This can be used to determine if certain types of endoscopes, or those used by certain individuals are more likely to require repair.

Such central control can also provide for an additional level of safety. If an endoscope (901) fails the test but is inadvertently returned to service, it may be the case where the medical personnel using the endoscope (901) will double check that the endoscope (901) has been cleared before using it by entering the serial number again at the starting point of the medical procedure into a computer on the network. In this situation, the serial number lookup at the central records area would indicate that the endoscope (901) should not be used and medical personnel can reject it for repairs and obtain a new scope before there is a possibility of the device harming a patient or from the device being additionally damaged.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for testing the integrity of an endoscope, the method comprising: obtaining an endoscope; supplying gas to an air enclosure which includes an internal volume of said endoscope to pressurize said air enclosure; sealing said air enclosure; measuring the pressure of said gas in said air enclosure over time; detecting an first rate of decrease in air pressure; recognizing a second rate of decrease in air pressure, said second rate being less than said first rate; discarding said first rate; comparing said second rate to a predetermined target rate to determine if said second rate is sufficiently high to indicate a leak in said endoscope; and in the following consecutive sequence of steps: instructing a user to manipulate said endoscope using a computer control system while said air enclosure is pressurized, the computer control system having an output device to instruct the user and an input device to indicate manipulation of the endoscope is complete said manipulation causing movement of said endoscope; indicating to said computer control system that said manipulation of said endoscope is complete; and re-measuring the pressure of said air enclosure after said manipulation is complete to indicate a presence of a leak in said endoscope.

2. The method of claim 1 wherein said instructing includes instructing manipulation of endoscope buttons.

3. The method of claim 1 wherein said instructing includes instructing manipulation of knobs which causes movement of endoscope tubing.

4. The method of claim 1 wherein said predetermined target rate is stored in a computer memory.

5. The method of claim 1 further comprising: identifying said endoscope as having been tested previously.

6. The method of claim 5 wherein said predetermined target rate is determined based on at least one previous test of said endoscope.

7. The method of claim 1, wherein in said measuring, said pressure of gas is 4 lbf/in$^2$.

8. The method of claim 1 further comprising: placing said endoscope in a holding device prior to said step of measuring.

9. The method of claim 8 wherein said holding device comprises a holding bin having a mat on its base, said mat including a plurality of fingers.

10. The method of claim 1, wherein said endoscope is manipulated by picking up the endoscope.

11. The method of claim 10, wherein said endoscope is manipulated when said computer control system is in a hold phase and pressure is measured during said manipulation.

* * * * *